United States Patent [19]

Diehr

[11] Patent Number: 5,453,506
[45] Date of Patent: Sep. 26, 1995

[54] PROCESS FOR THE PREPARATION OF 2-CHLORO-5-AMINOMETHYL-PYRIDINE

[75] Inventor: Hans-Joachim Diehr, Wuppertal, Germany

[73] Assignee: Bayer Aktiengesellschaft, Leverkusen, Germany

[21] Appl. No.: 86,603

[22] Filed: Jul. 1, 1993

[30] Foreign Application Priority Data

Jul. 6, 1992 [DE] Germany .......................... 42 22 152.8

[51] Int. Cl.$^6$ .................................................. C07D 213/61
[52] U.S. Cl. .......................................... 546/329; 546/286
[58] Field of Search ........................ 546/329, 286; 564/385, 415, 490

[56] References Cited

U.S. PATENT DOCUMENTS

| | | | |
|---|---|---|---|
| 4,499,097 | 2/1985 | Tomcufcik et al. | 514/341 |
| 5,360,650 | 4/1994 | Nabata | 546/329 |

FOREIGN PATENT DOCUMENTS

| | | | |
|---|---|---|---|
| 0425030 | 5/1991 | European Pat. Off. | 514/341 |
| 3726993 | 2/1989 | Germany | 546/329 |
| 4924969 | 5/1974 | Japan | 546/329 |
| 9213840 | 8/1992 | WIPO | 546/329 |

OTHER PUBLICATIONS

Chemical Abstract, vol. 81, No. 13, Abstract 77.810u, p. 452 (Sep. 30, 1974).
European Patent Office, Database WPI, Week 9236, Derwent Publications, AN–92–299951, JP 4247069, Koei Chem. Ind. Co. Feb. 4, 1991. (1 page).
European Patent Office, Database WPI, Week 8651, Derwent Publications, AN 86–336001, JP 61251663, Koei Chem. Ind. Nov. 8, 1986. (1 page).
European Patent Office, Database WPI, Week 7913, Derwent Publications, AN 79–24478B, JP 54022354, Sagami Chem. Res. Centre, Feb. 20, 1979. (1 page).
*Chemical Abstracts*, page 713, 27–Heterocycles, vol. 111, 1989; No. 173988s, "Preparation of the Antihypertensive Intermediate . . . ", F. Maurer, Bayer AG, Aug. 13, 1987.

*Primary Examiner*—C. Warren Ivy
*Assistant Examiner*—Zinna N. Davis
*Attorney, Agent, or Firm*—Sprung Horn Kramer & Woods

[57] ABSTRACT

Process for the preparation of 2-chloro-5-aminomethylpyridine of the formula (I)

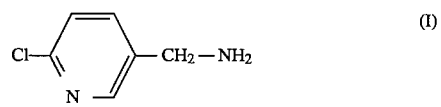

by a reaction of 2-chloro-5-cyano-pyridine of the formula (II)

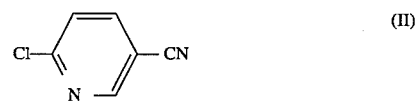

with hydrogen in the presence of ammonia and in the presence of an anhydrous metal catalyst, characterized in that the reaction is carried out in an apolar aprotic diluent at temperatures between 20° C. and 150° C.

3 Claims, No Drawings

PROCESS FOR THE PREPARATION OF 2-CHLORO-5-AMINOMETHYL-PYRIDINE

The invention relates to a novel process for the preparation of the known 2-chloro-5-aminomethyl-pyridine.

It is known that 2-chloro-5-aminomethyl-pyridine, an intermediate for the preparation of insecticides, is obtained when 2-chloro-5-cyano-pyridine is reacted with hydrogen in the presence of Raney nickel and ammonia in a reaction medium which contains water and, possibly, an organic solvent, at temperatures between 0° C. and 60° C. (compare DE-OS (German Published Specification) 3726993/LEA 25499).

However, yield and quality of this product in the process described are not totally satisfactory.

A process has now been for the preparation of 2-chloro-5-aminomethyl-pyridine of the formula (I)

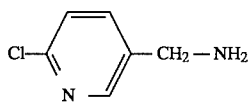
(I)

by a reaction of 2-chloro-5-cyano-pyridine of the formula (II)

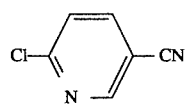
(II)

with hydrogen in the presence of ammonia and in the presence of an anhydrous metal catalyst, characterised in that the reaction is carried out in an apolar aprotic diluent at temperatures between 20° C. and 150° C.

It is considered surprising that the catalytic hydrogenation according to the process according to the invention, in the presence of an apolar aprotic diluent, that is without with use of water or another protic solvent, gives 2-chloro-5-aminomethyl-pyridine in a considerably improved yield in comparison with the known process.

The course of the reaction in the process according to the invention can be depicted by the following formula diagram:

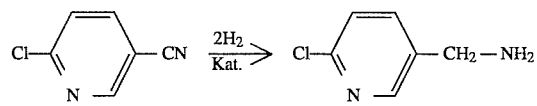

The 2-chloro-5-cyano-pyridine of the formula (II) to be used as starting material is already known (cf. J. Chem. Soc. [London] 1948, 1939–1945).

The process according to the invention is carried out in the presence of a metal catalyst. Raney catalysts are preferably used, such as for example Raney nickel or Raney cobalt. Raney cobalt is particularly preferred as the metal catalyst in the process according to the invention.

The process according to the invention is carried out in the presence of an apolar aprotic diluent. In this context these are understood to mean organic solvents which do not contain any easily detachable protons. These preferably include aliphatic and aromatic, nonhalogenated and halogenated, hydrocarbons such as hexane, heptane, octane and branched isomers thereof, and furthermore cyclohexane, methylcyclohexane, benzene, toluene, xylene, chlorobenzene and o-dichlorobenzene. Aromatic hydrocarbons are particularly preferred. Toluene and xylene and mixtures thereof may be mentioned in particular.

The reaction temperatures in the process according to the invention can be varied within a relatively large range. The procedure is generally carried out between 20° C. and 150° C. preferably between 50° C. and 120√ C., in particular between 80° C. and 110° C.

The pressure in the process according to the invention can likewise be varied within a relatively large range. The procedure is generally carried out in the pressure range between 1 and 200 bar, preferably between 20 and 150 bar, in particular between 50 and 120 bar.

To carry out the process according to the invention, for 1 mol of 2-chloro-5-cyano-pyridine of the formula (II), generally between 20 ml and 200 ml, preferably between 50 ml and 150 ml, of liquid ammonia and between 5 g and 50 g, preferably between 10 g and 30 g of a metal catalyst are used. The process according to the invention can be carried out by conventional hydrogenation methods.

In a preferred embodiment of the process according to the invention, the 2-chloro-5-cyanopyridine, the inert diluent, the metal catalyst and the ammonia are mixed in an autoclave and then, with the autoclave closed, hydrogen is added with an elevated internal pressure being established. The autoclave contents are then stirred at elevated pressure and elevated temperature until the reaction is completed.

The work-up can be carried out in a conventional manner. Preferably, the mixture is filtered off from the catalyst with suction and the solvent is carefully distilled off from the resulting filtrate in a water jet vacuum.

The remaining crude product can be purified by distillation under reduced pressure.

The 2-chloro-5-aminomethyl-pyridine of the formula (I) which can be produced by the process according to the invention can be used as an intermediate for the preparation of hypotensive agents (cf. U.S. Pat. No. 4499097) or insecticides (cf. EP-A 425030).

PREPARATION EXAMPLES

EXAMPLE 1

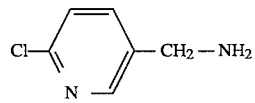

140 g (1.0 mol) of 2-chloro-5-cyano-pyridine, 700 ml of dried toluene, 25 g of dried Raney cobalt and 100 ml of liquid ammonia are mixed in an autoclave and then hydrogen is metered into the closed autoclave until an internal pressure of 70 bar is reached. The reaction mixture is then heated in the closed autoclave to 100° C. and stirred at this temperature for 8 hours (internal pressure: approximately 100 bar). After the autoclave is opened at room temperature, the mixture is filtered off with suction, the filter cake (catalyst) is washed using toluene and the diluent is carefully distilled off from the filtrate in a water jet vacuum.

130 g of a crude product are obtained which contain, according to gas chromatographic analysis, 91% of 2-chloro-5-aminomethyl-pyridine.

The yield in this case is 83% of theory.

EXAMPLE 2

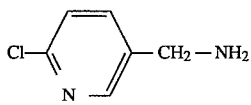

Example 2 is carried out analogously to Example 1, the Raney cobalt catalyst being replaced by the same weight of Raney nickel.

Yield: 79% of theory.

I claim:

1. Process for the preparation of 2-chloro-5-amino-methyl-pyridine of the formula (I)

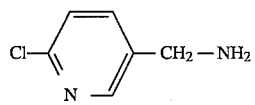

by a reaction of 2-chloro-5-cyano-pyridine of the formula (II)

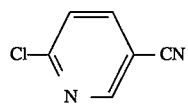

with hydrogen in the presence of ammonia and in the presence of an anhydrous Raney cobalt catalyst, wherein the reaction is carried out in an apolar aprotic diluent at temperatures between 20° C. and 150° C.

2. Process according to claim 1, wherein aliphatic or aromatic hydrocarbons are used as the diluent.

3. Process according to claim 1, wherein toluene or xylene is used as the diluent.

* * * * *